United States Patent [19]

Carapezza et al.

[11] Patent Number: 5,329,824
[45] Date of Patent: Jul. 19, 1994

[54] CENTRALIZER FOR INTERNAL PIPE INSPECTION DEVICE

[75] Inventors: Joseph R. Carapezza, Waltham; Linda T. Ystueta, Brighton, both of Mass.

[73] Assignee: Niagara Mohawk Power Corporation, Syracuse, N.Y.

[21] Appl. No.: 92,031

[22] Filed: Jul. 15, 1993

Related U.S. Application Data

[63] Continuation of Ser. No. 917,590, Jul. 17, 1992, abandoned.

[51] Int. Cl.$^5$ ............................................. G01B 5/12
[52] U.S. Cl. ................................................. 73/866.5
[58] Field of Search .............. 73/623, 865.8, 866.5; 250/261, 265; 358/100; 166/250, 253–255, 241.1, 241.5, 241.6; 324/220, 221; 367/25, 35, 911; 181/102, 105; 175/40, 50

[56] References Cited

U.S. PATENT DOCUMENTS

| 1,130,775 | 3/1915 | Toffey | 254/134.3 |
|---|---|---|---|
| 1,666,980 | 4/1928 | Sharp | 254/134.3 |
| 1,751,415 | 3/1930 | McCaffrey | 254/134.3 |
| 2,122,697 | 7/1938 | Potter | 33/205 |
| 2,219,555 | 10/1940 | Burwell | 15/104.18 |
| 2,499,456 | 3/1950 | Browne | 166/241.1 |
| 3,267,366 | 8/1966 | Bricaud | 324/221 |
| 3,267,967 | 8/1966 | Guthrie | 138/97 |
| 3,439,527 | 4/1969 | Rohrer | 73/40.5 |
| 3,555,689 | 1/1971 | Cubberly, Jr. | 166/241.5 |
| 3,612,487 | 10/1971 | Raney | 254/174 R |
| 3,718,978 | 3/1973 | Van Koevering et al. | 33/174 L |
| 3,978,924 | 9/1976 | Roesner | 166/241.5 |
| 4,090,534 | 5/1978 | Martin et al. | 138/97 |
| 4,197,908 | 4/1980 | Davis et al. | 166/55 |
| 4,201,597 | 5/1980 | Armstrong et al. | 134/167 R |
| 4,253,497 | 3/1981 | Martin et al. | 138/97 |
| 4,261,204 | 4/1981 | Donaldson | 73/421.5 R |
| 4,497,332 | 2/1985 | Sewell et al. | 137/15 |
| 4,523,640 | 6/1985 | Wilson et al. | 166/241.1 |
| 4,538,316 | 9/1985 | Reinhart et al. | 15/104.06 R |

(List continued on next page.)

FOREIGN PATENT DOCUMENTS

| 714889 | 8/1965 | Canada | 166/241.6 |
|---|---|---|---|
| 0085504 | 10/1931 | European Pat. Off. | |
| 0083759 | 12/1982 | European Pat. Off. | |
| 2637043 | 3/1990 | France | |
| 50255 | 4/1977 | Japan | |
| 188579 | 8/1988 | Japan | |
| 0300958 | 12/1988 | Japan | 73/866.5 |
| 57964 | 2/1990 | Japan | |
| 83/03457 | 10/1983 | PCT Int'l Appl. | |
| 680094 | 8/1979 | U.S.S.R. | |
| 1263717 | 2/1972 | United Kingdom | |
| 2144009 | 2/1985 | United Kingdom | |
| 2172079 | 9/1986 | United Kingdom | |

OTHER PUBLICATIONS

Inspection Systems & Services Brochure, PLC International, Mar., 1989, 4 pages.

(List continued on next page.)

*Primary Examiner*—Robert Raevis
*Attorney, Agent, or Firm*—Heslin & Rothenberg

[57] ABSTRACT

Internal pipe inspection apparatus is disclosed having a novel collapsible centralizer mechanism for an in-line pipe inspection head. The inspection apparatus is insertable into different size pipelines through a small, lateral service opening. The apparatus includes a compact inspection pipe head having a viewing assembly for imaging the interior of the pipe. The head is sized to pass through a standard lateral service opening substantially less in diameter than the diameter of the pipe. Various collapsible centralizing members are described for positioning the pipe inspection head viewing assembly substantially concentric with an axis of the pipe. The novel centralizers include multiple bendable support legs which are pivotally connected at different points to the inspection device such that each leg forms a substantially sinusoidal shape when extended and each leg collapses close to the inspection head and trailing ferrules when retracted for insertion into (or removal from) the pipe. The sinusoidal-shaped legs are selectively biased to their extended positions.

33 Claims, 7 Drawing Sheets

U.S. PATENT DOCUMENTS

| | | | |
|---|---|---|---|
| 4,646,787 | 3/1987 | Rush et al. | 138/98 |
| 4,651,559 | 3/1987 | Horigome et al. | 73/40.5 R |
| 4,664,791 | 2/1987 | Sonoda et al. | 73/432.1 |
| 4,690,006 | 9/1987 | Urata | 73/866.5 |
| 4,779,469 | 10/1988 | Evans et al. | 82/82 |
| 4,843,896 | 7/1989 | Nepeloni et al. | 73/866.5 |
| 5,025,670 | 6/1991 | McNulty et al. | 73/865.8 |
| 5,084,764 | 1/1992 | Day | 73/865.8 |
| 5,174,164 | 12/1992 | Wilheim | 73/866.5 |

OTHER PUBLICATIONS

Minicamera Inspection System Brochure, PLS International, Mar. 13, 1989, 4 pages.

World's Leading Manufacturer of Sewer Line Inspection and Joint Sealing Equipment—Cues, Mar., 1989, 23 pages.

Solid State Television Inspection System, Pierpoint Flexiprobe, 1987, 8 pages.

TV Inspection System FS 5030 A, Avanti International, 1988–1989, 4 pages.

TV Inspection System FS 5026 A, Avanti International, 1988, 2 pages.

TV Inspection System FS 5028 A, Avanti International, 1988, 2 pages.

Compact Color TV Camera, Osaka Gas Engineering (date unknown), 2 pages.

Model 1065 Sewer-Raider Electric Sewer Cleaner, Spartan Tool (date unknown), 2 pages.

Mini Camera—Televisioning Systems for Mainline Sewers, Service Laterals and Industrial Inspection, Aries Industries, Inc., Apr. 1991, 6 pages.

fig. 1 fig. 4 fig. 5 fig. 13 fig. 8

CENTRALIZER FOR INTERNAL PIPE INSPECTION DEVICE

This application is a continuation of application Ser. No. 07/917,590, filed Jul. 17, 1992, now abandoned.

CROSS-REFERENCE TO RELATED APPLICATION

This invention relates to a co-pending patent application, U.S. Ser. No. 07/523,323, filed May 14, 1990, and assigned to the same assignee. This co-pending application is hereby incorporated herein by reference.

BACKGROUND OF THE INVENTION

1. Technical Field

This invention presents devices and methods for inspection and repair of piping, such as fluid distribution means, and more particularly, devices and methods for inspecting gas mains without interrupting gas service during the testing operation. Certain novel collapsible support mechanisms (or centralizers) for such an inspection device are specifically described herein.

2. Description of the Prior Art

The transportation of natural gas, water, petroleum products, and other gases and fluids typically involves the use of pipelines, often of considerable lengths. Cross-country pipelines are, of course, of large diameters such as 12 inches, 24 inches and 30 inches in capacity. Such pipeline sizes are usually associated with the transporting of natural gas, and large sizes of pipes are normally fabricated of steel. In urban areas distribution of natural gas, and the distribution of manufactured gas in previous years, is accomplished through vast networks of smaller size buried pipe, principally of four, six, eight and ten inch diameters. While present installation of underground pipe utilizes plastic, particularly natural gas pipes of four, six and eight inch diameter size, thousands of miles of cast iron and steel pipe have been installed and buried over the years, and are presently in use for the delivery of natural gas. In most of the United States cast iron and steel gas distribution lines are often four inches in diameter and typically include many 90 degree corners. Common problems encountered with buried cast iron and steel pipe include deflection of the pipe caused by settling of the earth around the pipe, heaving due to frost (or forces applied to the earth around the pipe) causing leaking at joints or cracking of the line and, often, the collection of water therein. In addition, corrosion leaks in steel mains are common.

While numerous devices exist for the visual or other inspection of the interior of a pipeline, most, if not all, existing techniques have disadvantages which make their use at best inconvenient and, in all likelihood, difficult, time consuming and/or expensive. Many in-line pipe inspection devices and methods require, for example, in the case of gas pipe lines, discontinuance of service and/or severing of the main for insertion of the inspection device into an open end of the main, which is a complicated and costly process involving bypass and shut-off procedures. Obviously, this technique is expensive both in terms of the interruption to the gas service and the damage caused to the gas main. Inspection devices so inserted typically include a fixed centralizer feature for maintaining the in-line viewing assembly substantially concentric with the axis of the pipe.

In the above-incorporated application, entitled "Internal Pipe Inspection System," a collapsible centering mechanism is described for supporting the device inspection/repair head once inserted into a gas main. The novel inspection/repair head disclosed therein is inserted into a live gas main (without requiring an interruption of service to customers connected to the line) through an opening, such as an existing lateral service opening, in the line smaller than the internal diameter of the pipeline. To accomplish this object it is essential that the support mechanism for the inspection/repair head be readily collapsible and/or bendable. The extent of collapsibility is particularly significant for gas mains since lateral customer service lines typically tap into a main line via an opening that is one-third or less the size of the internal diameter of the pipeline. For example, one inch and one and one-quarter inch diameter lateral openings are common in four inch and six inch gas distribution mains in the United States.

One preferred centering technique described in the incorporated application is the use of rigid, outwardly biased legs extending from the central inspection/repair head and pivotally secured to the body so as to manually collapse thereto. If desired, skids can be hingedly secured to the free ends of the outwardly extending legs, again so as to collapse towards the main inspection/repair head when manually actuated (i.e., upon insertion and removal of the inspection/repair head through a restricted opening in the pipe). Various other centering approaches are also described therein.

Continuing research into an internal pipe inspection device such as described in the incorporated application has resulted in an improved support mechanism (centralizer) having a low profile mounting, simple design and ready adjustability to pipes of different internal diameter. This commercially significant design is a principal aspect of the present disclosure.

DISCLOSURE OF THE INVENTION

Briefly summarized, one aspect of the present invention describes a collapsible support mechanism for a pipe inspection device having an inspection head and a trailing hose section. The collapsible mechanism includes a plurality of bendable support legs, each of which is pivotally secured at a first end to the inspection head. Two ferrules slidably encircle the hose, with one of the two ferrules disposed nearer to the inspection head than the other. Each bendable support leg is pivotally secured between its first end and its second end to the ferrule nearer the inspection head and at its second end to the ferrule further from the inspection head so that when the ferrules are positioned near the inspection head, the support legs are pivoted outwardly from the inspection head and when the ferrules are located away from the inspection head, the support legs are collapsed towards the inspection head. A biasing mechanism for maintaining the support legs in their extended, operational position is also included. When in the extended position, the support legs preferably define a substantially sinusoidal shape.

In another embodiment, a collapsible centering mechanism for a pipe inspection device insertable into a pipeline through a lateral opening smaller than an internal diameter of the pipeline is provided. The inspection device includes an in-line inspection head and a hose section trailing therefrom. The centering mechanism has at least three bendable support legs each of which has a first end and a second end. Each support leg is pivotally secured to the inspection head near its first end. A ferrule slidably encircles the hose section and each support leg is pivotally secured to the ferrule adjacent its second end such that when the ferrule is disposed at a first location along the hose near the inspection head the supporting legs extend outwardly from the inspection head to support the device, and when the ferrule is disposed at a second location along the hose section away from the inspection head the support legs are collapsed towards the inspection head to facilitate the inspection device's insertion into or removal from the pipeline through the restricted lateral pipe opening. Preferably, a biasing mechanism is provided for biasing the support legs in the outwardly extended position so that the legs extend automatically when the inspection device is positioned within the pipeline.

In a more comprehensive embodiment, the present invention comprises a pipe inspection apparatus insertable into a pipeline for inspection or repair thereof. The apparatus includes a compact pipe inspection head including a central body portion which has a viewing assembly for imaging the interior of a pipeline when the inspection head is positioned therein. A flexible hose section is connected to trail the central body portion and multiple bendable support legs having a first end and a second end are secured about the central body portion and hose section. Each support leg pivotally connects to the central body portion adjacent its first end. At least two ferrules slidably encircle the hose section, with a first ferrule being closer to the central body portion than a second ferrule. Each support leg pivotally connects adjacent its second end to the second ferrule and preferably pivotally connects to the first ferrule intermediate its first end and second end. A biasing mechanism for extending the multiple bendable support legs outwardly once positioned within a pipeline is also provided. When extended, each support leg defines a substantially sinusoidal shape such that multiple contact support points to the interior surface of the pipeline are provided by the support legs.

To summarize, certain novel centralizers for an in-line pipe inspection device are described herein. These centralizers provide exceptional performance in terms of camera centralization, ease of use, and restricted lateral service entrance capabilities. Design advantages include a low profile mounting, simplistic composition, (low total number of parts) variable pipe size capabilities, ease of replacement, and low cost. In addition to the described centralizer, a preferred camera assembly is also presented. This camera assembly eliminates picture degradation caused by raw signal transmission through long lengths of cable, enables existing pipe inspection hardware to be utilized to support the head unit and provides a simpler means of adapting future state-of-the-art camera technologies to the inspection device of the present invention.

BRIEF DESCRIPTION OF THE DRAWINGS

These and other objects, advantages and features of the present invention will be more readily understood from the following detailed description of certain preferred embodiments of the present invention, when considered in conjunction with the accompanying drawings in which.

DETAILED DESCRIPTION OF THE INVENTION

Reference is now made to the drawings in which the same (or similar) reference numerals are used throughout the different figures to designate the same (or similar) components.

Figure 1:
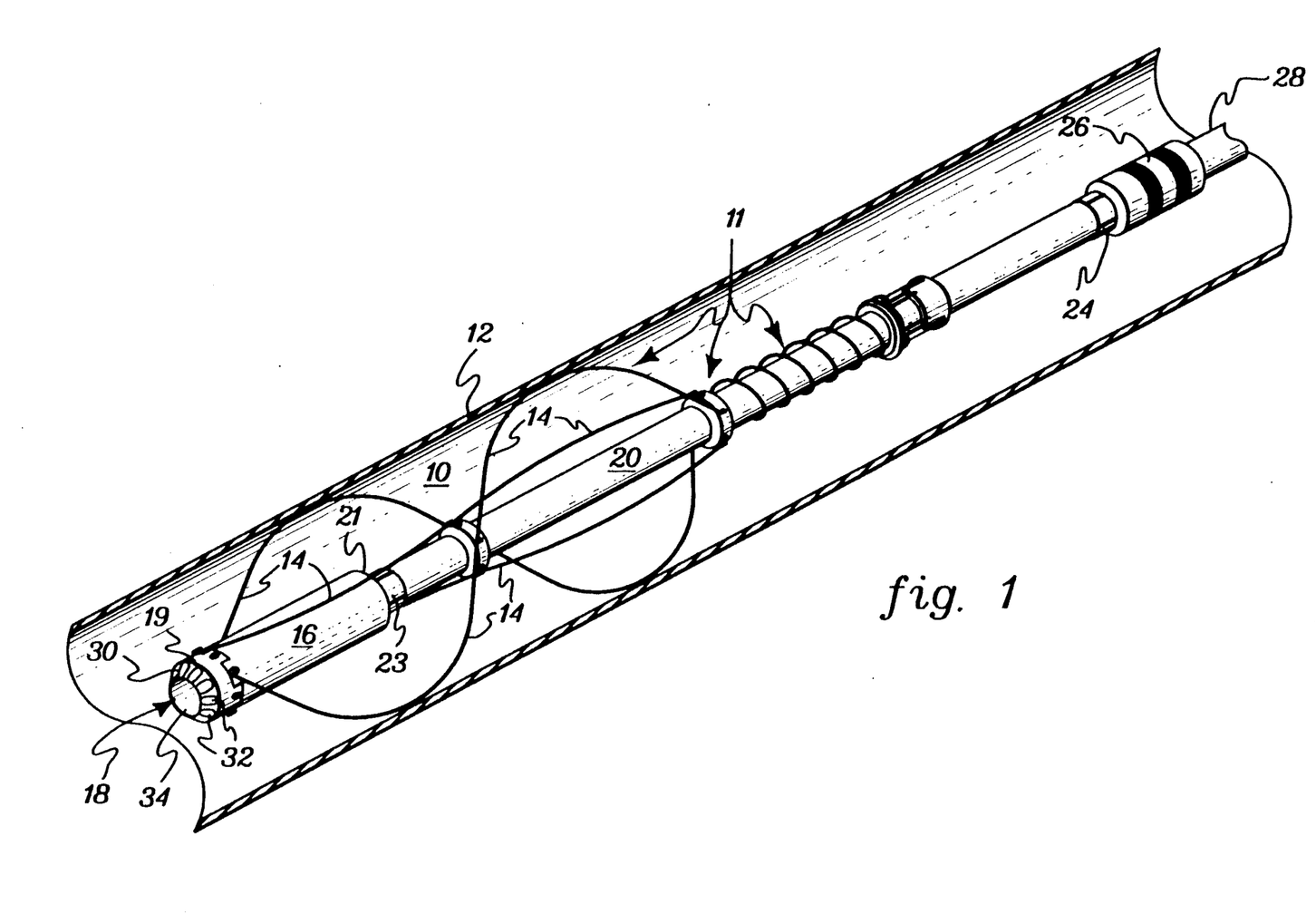
FIG. 1 is a partial perspective view of a pipe inspection device pursuant to the present invention, shown in operation within a partially cutaway pipeline.

One embodiment of a novel pipeline inspection device is described in the above-incorporated application. Building thereon, important elements of a pipe inspection device pursuant to the present invention, generally denoted 10, are shown in FIG. 1.

Device 10, disposed within a partially cutaway pipeline 12, is shown in an operational position with its support legs 14 extended. The inspection device includes an inspection head 16 having a viewing assembly 18 at one end 19 thereof and a flexible hose or cable section 20 secured to its other (trailing) end 21. (The term "hose" as used herein means any hose, cable, tube, or other such similar structure.) Hose 20 is hollow to accommodate wiring for viewing assembly 18 to connect to an operator control/display unit (not shown) located, for example, above ground. Hose section 20 may be crimped 23 to inspection head 16. At its other end hose 20 is crimped 24 to an electrical/mechanical coupling 26 which connects hose 20 to a flexible hollow tube 28 (e.g., 200' in length) containing electrical wiring for transmitting control/display signals between the viewing assembly and the control/monitor unit. Tube 28 and coupling 26 can comprise commercially available items. For example, the flexible one-piece push cable and camera to cable connector of the Mini Camera Televising System marketed by Aries Industries, Inc. of Sussex, Wis., could be used. (As an alternative to the hose/coupling/tube configuration of FIG. 1, a cable could couple directly into inspection head 16.)

A centralizer 11 includes multiple support legs 14 which, together with a biasing mechanism, maintain inspection head 16 substantially concentric with the axis of pipeline 12. Various alternate embodiments for the centralizer, and in particular, mechanisms for biasing support legs 14 to an operational, extended position are described in detail below with reference to FIGS. 2-13.

The inspection device is designed to detect cracks or leaks within the wall of pipe 12 a significant distance from the point of introduction of the inspection head into the pipe, for example, up to 200 feet away. Other uses include generalized inspections, searching for water or ice induced blockages, and close inspection of bell joints and service tees. Non-inspection type uses of the apparatus, and in particular, inspection head 16, are conceivable by those skilled in the art.

As noted, a viewing mechanism 18 is disposed within inspection head 16. The viewing mechanism preferably includes a state-of-the-art type camera assembly such as a CCD surveillance camera assembly and an illumination system having a plurality of lights 32 surrounding the lens 34 of the camera. Any one of numerous such cameras (and their specifications) are readily available to those skilled in the art. Several such systems are described in the above-incorporated application. A presently preferred camera, however, is manufactured by Pulnix of Sunneyvale, Calif., and marketed as model Pulnix TM-7X. This camera provides advantages in package size and enables the entire camera assembly to be disposed within the inspection head, thereby eliminating picture degradation otherwise caused by raw signal transmission through the extended lengths of cable (i.e., hose 20 and tube 28). Further, use of this camera assembly provides a simpler means for adapting future state-of-the-art camera technologies to the in-line inspection device.

As noted in the incorporated application, a significant object of the inspection device is to attain an intrinsically safe system for inspecting the interior walls of a live gas main. The above-noted camera assembly and the illumination system described in the incorporated application can satisfy intrinsic safety requirements with certain modifications. Intrinsic safety (IS) strategy could consist of adding resistors (for example, 30 ohms) at each camera/powerline interface and an IS barrier on each camera and lighting line. The object is to limit the energy release potential of the inspection system when in a live natural gas pipeline. The balance is to maintain appropriate power levels to the camera while also remaining below power and energy levels capable of causing ignition within the line.

For example, a total of four IS barriers may be needed for insuring safety. Three barriers would be for the camera and lamp power lines, while the fourth would be for the video line. In the case of the camera power barriers, component selection is based upon obtaining the largest current limiting resistor values which would allow the necessary power to be supplied to the camera. Again, in each barrier design, care must be taken to keep the maximum achievable current levels to a minimum so that the combination of barrier designs is unable to be used together without special precautions against one fault current ganging.

An intrinsically safe characteristic advantageously allows inspection device 10 to safely operate to inspect the interior surface of a live gas main, and in particular, small four inch and six inch gas mains. As a further advantage of the present invention, damage to a main is minimized by inserting, controlling and removing the in-line inspection device through a conventional lateral service opening. Such an opening typically has a diameter smaller than the inner diameter of the pipeline. (Alternatively, with the present invention a lateral pipe opening can be drilled with any standard service tapping equipment, an option which represents an important advantage.)

Thus, the prior need to "break" a gas main for insertion of the inspection device is avoided, as are complicated bypass and shut-off procedures. Since the main is live, natural gas leakage through the lateral opening can be reduced by using a closed cell rubber seal or gasket (not shown) to surround tube 28 (FIG. 1) at the opening (not shown). Such a material would inhibit the escape of natural gas from the main. In operation, after insertion of inspection device 10 within pipeline 12 through the lateral opening, the sealing gasket could then be clamped in place by use of chain pipe clamps (not shown), which are well known in the art.

The present disclosure also encompasses certain new centering mechanisms for positioning the inspection device's head (including the viewing mechanism) substantially concentric with the central axis of the pipeline. Various such centralizer embodiments are next described.

Figures 2, 3:
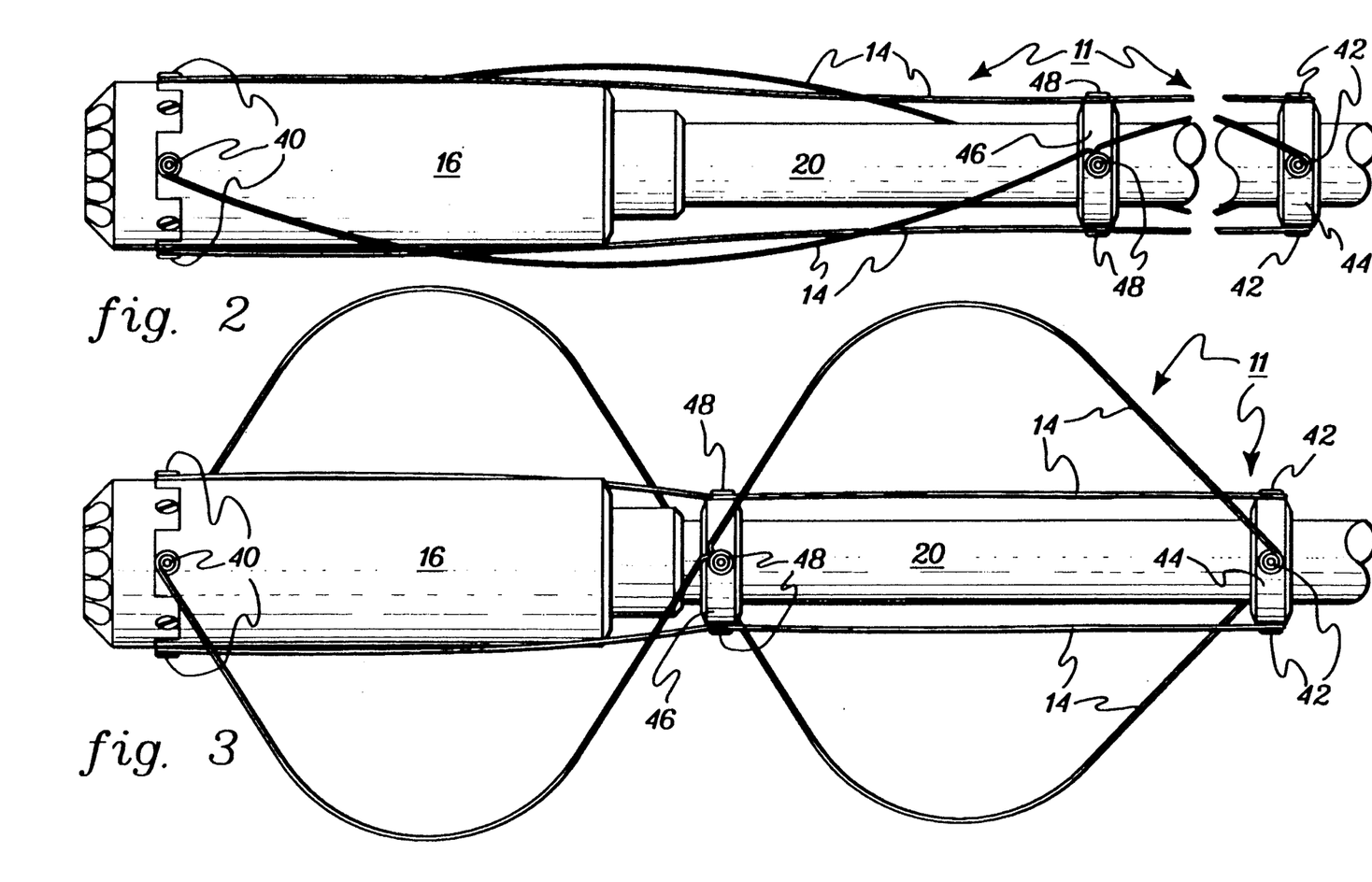
FIG. 2 is an enlarged elevational view of the inspection/repair head portion of the device of FIG. 1, shown with its support legs in a collapsed state.
FIG. 3 is an elevational view of the enlarged structure of FIG. 2, shown with the support legs in an extended, operational position.

Referring first to the expanded views of FIGS. 2 and 3, multiple support legs 14 are arranged about the circumference of device 10. (Four support legs are shown.) Each leg is pivotally secured to the inspection head at a spaced location such that the legs are arranged substantially symmetrically about the circumference of the device. As shown, one end of each support leg 14 pivotally connects 40 to inspection head 16, and the other end pivotally connects 42 to a movable ferrule 44 encircling hose 20. Preferably, a second ferrule 46 (also surrounding hose 20) provides a central pivoting connect point 48 for each leg 14.

FIG. 2 partially shows device 10 with support legs 14 collapsed towards the device, for insertion of the device into and/or removal from pipeline 12 through a lateral opening (not shown) of a diameter smaller than an internal diameter of the pipeline. FIG. 3 depicts support legs 14 in an operational, extended position for supporting inspection device 10 within a pipeline (not shown). As can be seen from the figures, each support leg 14 preferably obtains a substantially sinusoidal shape when extended from the inspection head and trailing hose section for centering of the device within the pipeline.

Figure 4:
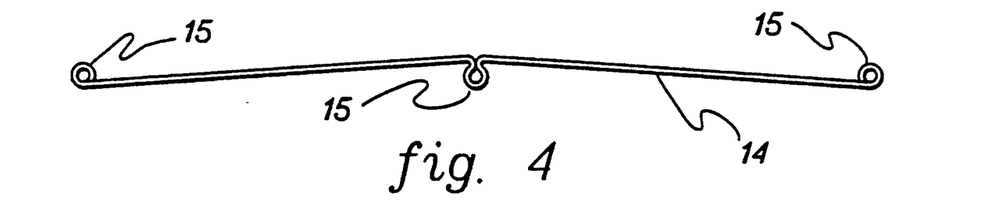
FIG. 4 is a plan view of one embodiment of a support leg for the structure of FIGS. 1-3.

FIG. 4 shows one preferred embodiment for a support leg 14 wherein a circle or ring shape 15 is defined at each pivot point, i.e., at each end and near the middle of the leg. Leg 14 of FIG. 4 can be fabricated of a bendable wire material such that the pivot points are formed in a common plane with the balance of the wire material disposed between the points. Three pivotal contact points are preferred to define a sinusoidal shape for each extended leg, both to ensure balance of the inspection device about an axis central to the pipeline (since there are multiple contact points) and to allow the support legs to independently bend or move whenever an obstruction is encountered within the pipeline. (Obviously, additional pivot points could be added to continue the sinusoidal shape or, alternatively, only two pivot points could be used with a plurality of legs to support the inspection head.)

Figure 5:
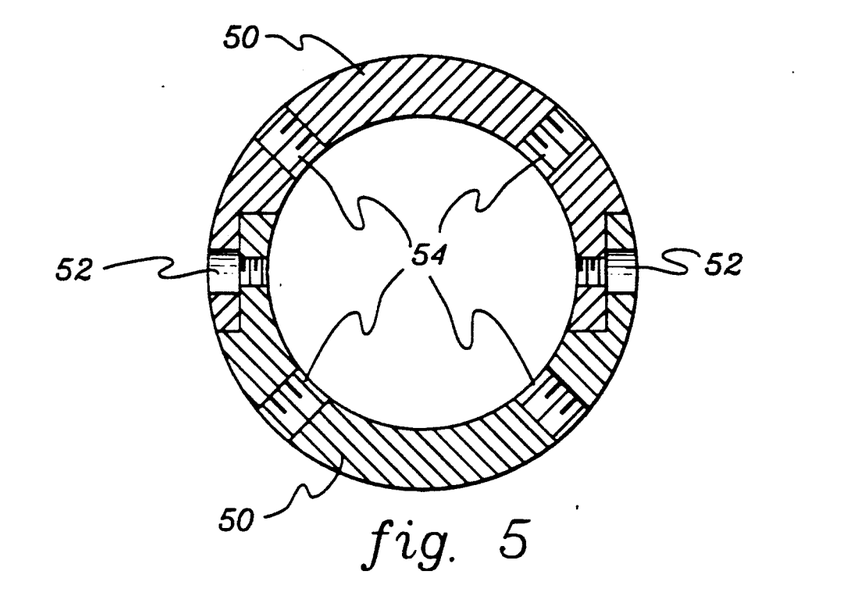
FIG. 5 is a cross-sectional view of one embodiment of a ferrule for the structure of FIGS. 1-3.

A cross-sectional view of one embodiment of a ferrule (44/46) is shown in FIG. 5. As depicted, each ferrule is constructed of two identical semicircles 50, which are joined together by connecting screws (not shown) disposed within threaded openings 52 to form the ferrule. Construction of ferrules 44 and 46 from identical halves allows either ferrule to be subsequently removed from hose 20 for repair or replacement. (Again, hose section 20 is secured (e.g., by crimping) to the inspection head 16 at one end and to mechanical/electrical coupler 26 at the other end (see FIG. 1).) The pivot connections 42 and 48 to ferrules 44 and 46, respectively, may comprise screws loosely passing through the appropriate ring 15 (FIG. 4) in the corresponding leg 14 and secured to the respective ferrule in one of a plurality of thread openings 54.

Figure 6:
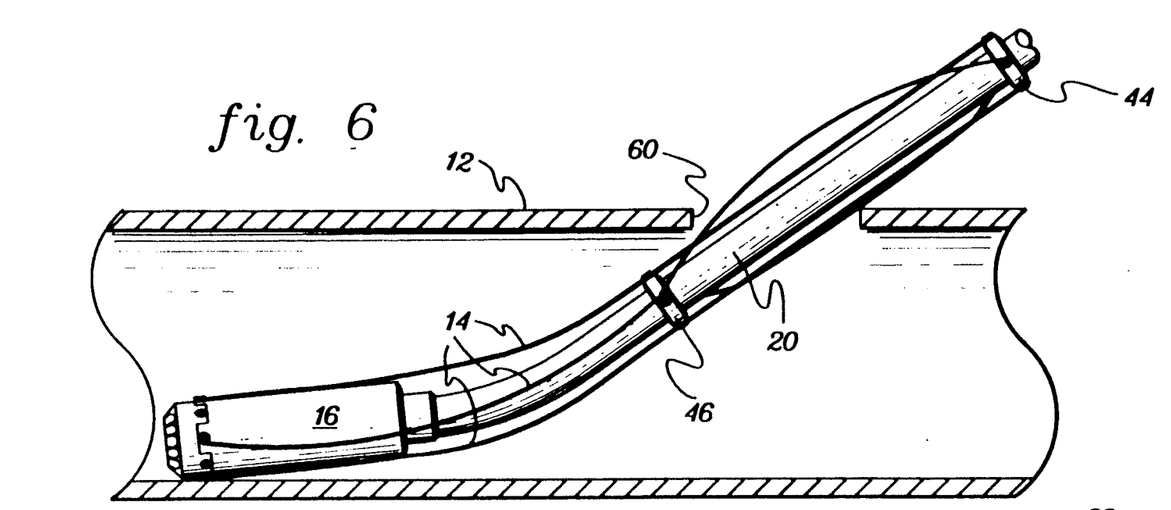
FIG. 6 is an elevational view of the collapsed structure of FIG. 2 being inserted into (or withdrawn from) a pipeline through a lateral opening of diameter smaller than the internal diameter of the pipeline.
Figure 7:
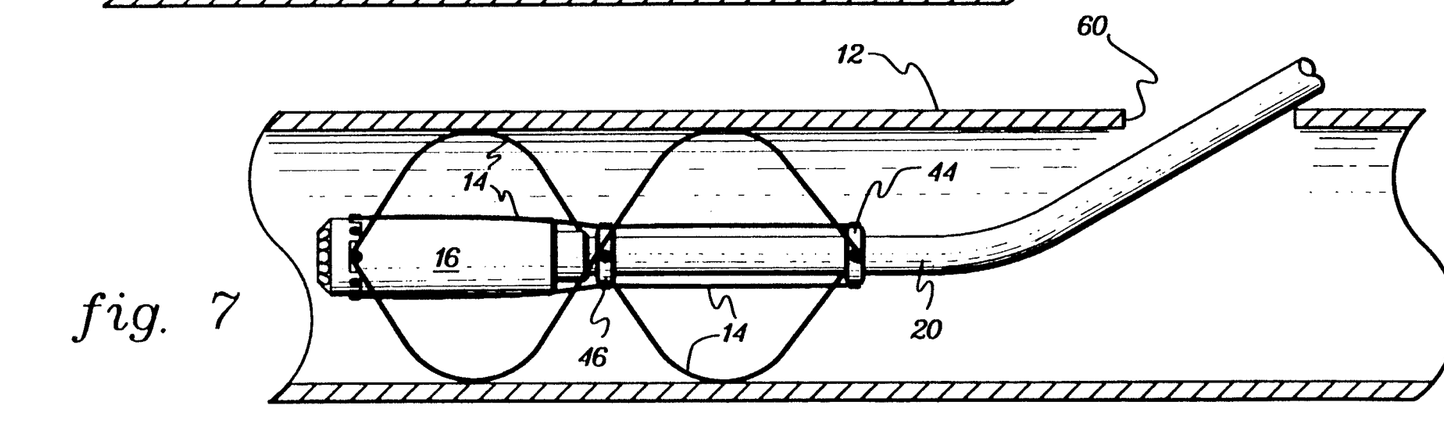
FIG. 7 is an elevational view of the expanded structure of FIG. 3 disposed within a pipeline for inspection thereof.

The structure of FIG. 2, with supporting legs 14 collapsed towards head 16 and hose 20 is shown in FIG. 6 being inserted into (or removed from) a pipeline 12 through a lateral service opening 60. As shown, reciprocating ferrules 44 and 46 are remotely disposed along hose 20 relative to head 16 when centralizing legs 14 are collapsed. In comparison, an operational, extended position for legs 14 is shown in FIG. 7, wherein ferrules 44 and 46 are disposed proximate to inspection head 16. By relocating the ferrules as noted, the supporting legs have pivoted from the collapsed position of FIG. 6 to the extended position of FIG. 7, such that the legs now contact an inner wall of the pipeline at the outer points of their sinusoidal shapes. Obviously, this ability to contact depends also on the size of the legs. Typical leg lengths of 16 to 18 inches are preferred to accommodate both 4 inch and 6 inch diameter pipelines. Further, depending upon the size of the supporting legs and the diameter of the pipeline, the legs may flatten somewhat where contact to the inner surface of the pipeline is made.

In one embodiment, each supporting leg could be fabricated to have a preformed sinusoidal shape, i.e., possess an internal bias when in a free state which results in the leg forming a sinusoidal shape (such as shown in FIG. 7). The collapsed state (shown in FIG. 6) is obtained by manually pulling, for example, the aft ferrule 44 (and with it ferrule 46) away from inspection head 16 until the legs are fully collapsed towards the inspection head and hose. When released, the internal biasing of each leg returns the centralizer to the operational position depicted in FIG. 7. Two additional biasing mechanisms are described below, a first with reference to FIGS. 9 and 10, and a second with reference to FIGS. 11-13. With either embodiment, the supporting legs could also have an internally biased sinusoidal shape when in a free state.

Figure 8:
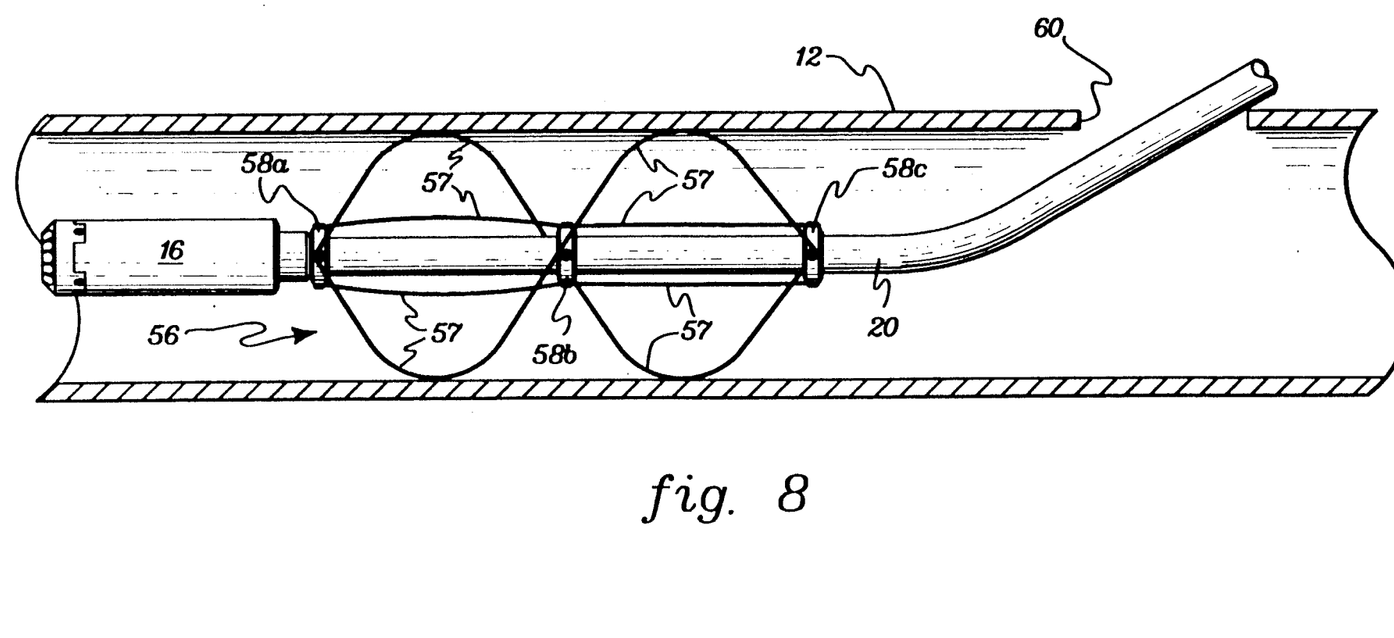
FIG. 8 is an elevational view of a further embodiment of a centralizer pursuant to the present invention, shown with the centralizer in an operational, extended position within the pipeline.

Before discussing the alternate biasing mechanisms of FIGS. 9-13 however, refer to FIG. 8 wherein an alternative location for a centralizer denoted 56 pursuant to the present invention is shown. Centralizer 56 comprises multiple support legs 57 which, together with a biasing mechanism (not shown), function to maintain inspection head 16 substantially concentric with the axis of pipeline 12. Centralizer 56 also includes three ferrules 58a, 58b and 58c which slidably encircle hose 20 secured to inspection head 16. Each bendable support leg is pivotally connected to ferrules 58a and 58c adjacent each of its ends and to ferrule 58b approximately at a center location such that when the legs are flexibility bent and pivoted to extend outwardly as shown, each leg forms a substantially sinusoidal shape. One or more stop mechanisms (not shown) could be used around hose 20 to insure that ferrules 58a, 58b and 58c surround hose 20 at a location adjacent inspection head 16. (In order to maintain the viewing assembly of the inspection head substantially concentric with the axis of pipeline 12, centralizer 56 is preferably disposed adjacent the inspection head.)

Figures 9, 10:
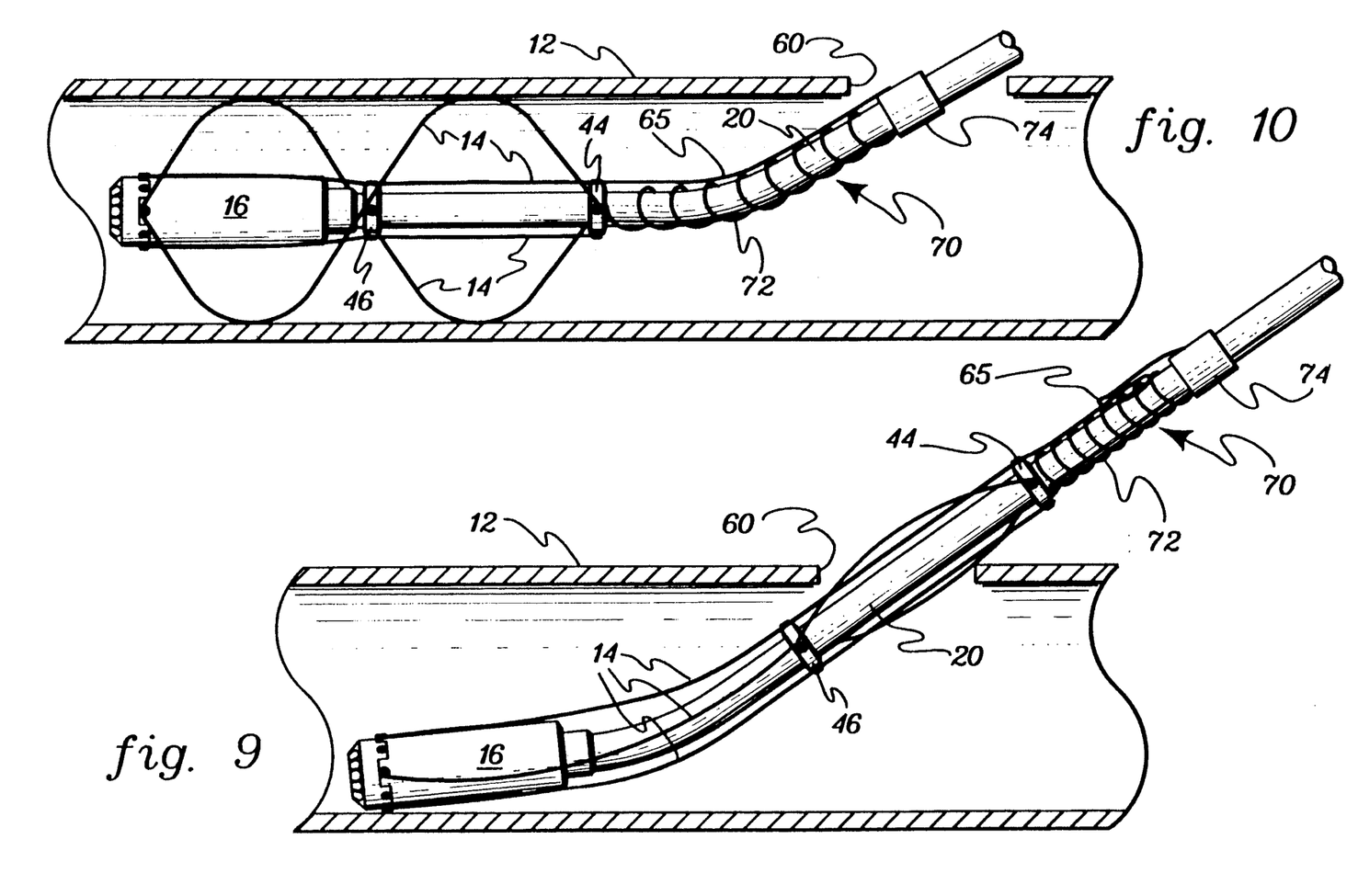
FIG. 9 is an elevational view of another embodiment of a centralizer pursuant to the present invention, with the spring biasing mechanism compressed and the legs collapsed for insertion into (or withdrawal from) a lateral opening of diameter smaller than an internal diameter of the pipeline.
FIG. 10 is an elevational view of the structure of FIG. 9, shown with the centralizer in an operational, extended position within the pipeline.

Referring now to FIGS. 9 and 10, support legs 14 are again spaced substantially symmetrically about the circumference of the inspection device with each leg 14 being pivotally connected at one end to inspection head 16 and at the other end to movable ferrule 44, along with having a center pivotal connection to ferrule 46. A biasing mechanism 70 is also provided. Mechanism 70 comprises a spring 72 and a fixed stop 74. Stop 74 encircles hose 20 at a fixed location along the hose. To attain a collapsed position (such as shown in FIG. 9), the aft ferrule 44 is manually actuated towards stop 74, thereby compressing spring 72 and collapsing support legs 14 towards the inspection head and hose. Once positioned within pipe 12, aft ferrule 44 is released allowing spring 72 to expand, moving ferrules 44 and 46 towards inspection head 16, and thereby returning support legs 14 to a sinusoidal shape (FIG. 10). To retrieve the inspection device the process is simply reversed, i.e., when the aft ferrule 44 becomes accessible through opening 60, it is pulled backwards, thereby compressing spring 72 against stop 74 and collapsing legs 14 towards inspection head 16 and hose section 20. (If desired, a lanyard 65 connecting ferrule 44 and stop 74 may be included to facilitate collapsing of legs 14 by an operator when withdrawing the device from a pipeline.) As a practical example, in the fixed stop embodiment spring 72 may be 10 to 12 inches (25-30 cm) in length.

Figures 11, 12:
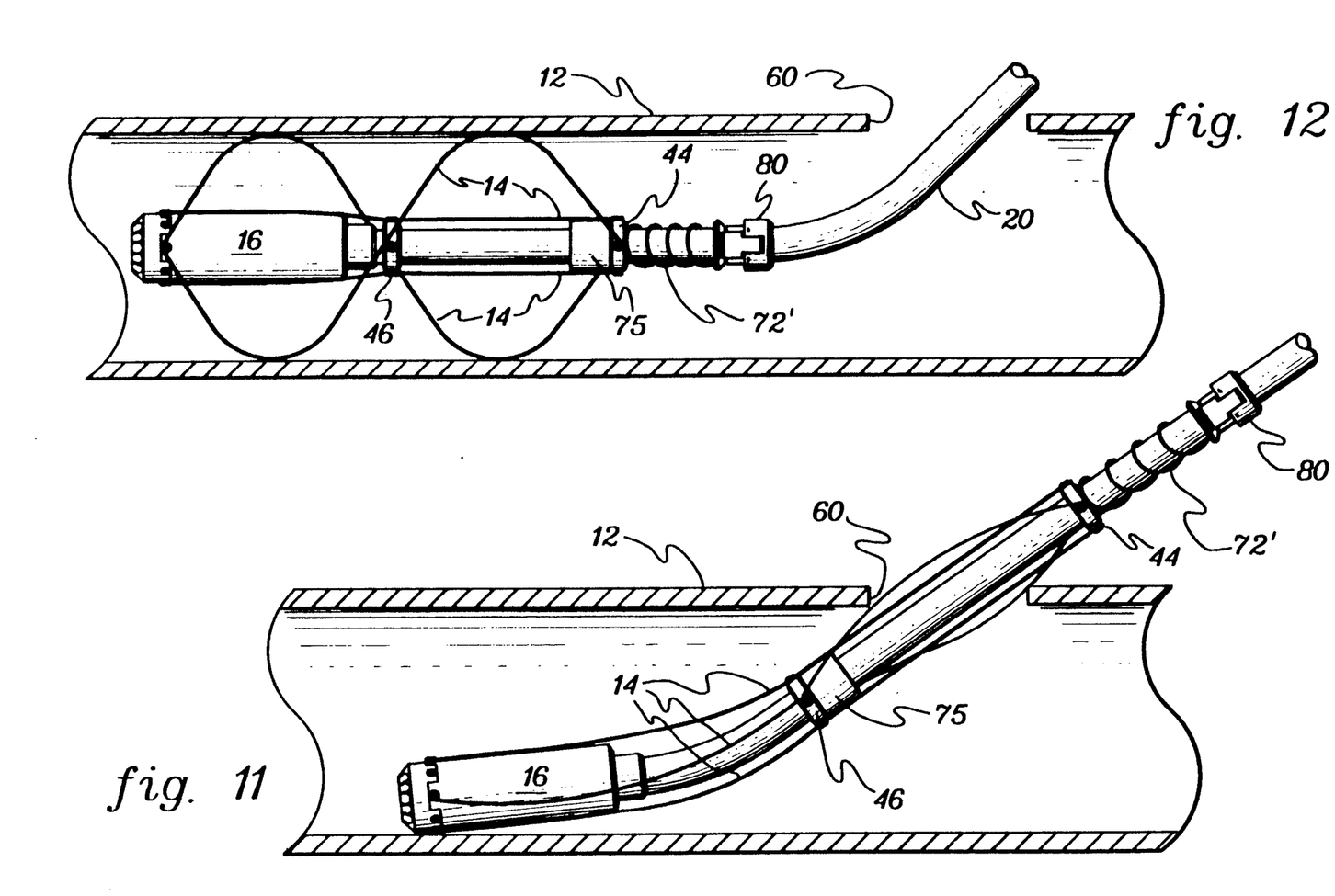
FIG. 11 is an elevational view of yet another embodiment of a centralizer pursuant to the present invention, shown with the support legs in a collapsed position for insertion into or removal from the pipeline.
FIG. 12 is an elevational view of the structure of FIG. 11, with the support legs shown in an operational, extended position within the pipeline.
Figure 13:
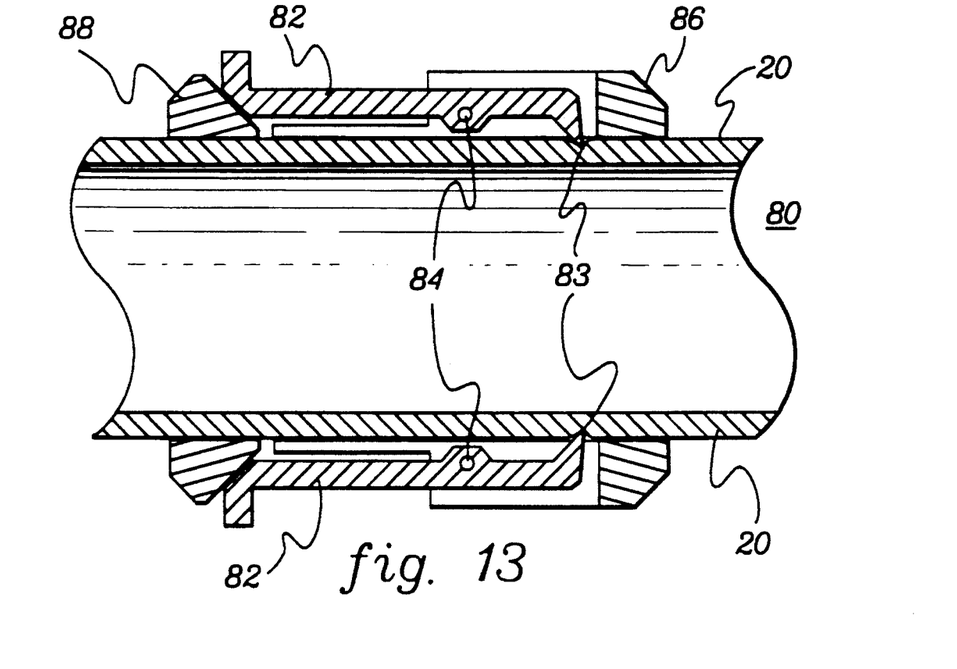
FIG. 13 is a cross-sectional view of one embodiment of a movable stop for the leg biasing mechanism of FIGS. 11 and 12.

Another embodiment of a centralizer pursuant to the present invention is depicted in FIGS. 11-13. The difference between this centralizer embodiment and the embodiment of FIGS. 9 and 10 is that the stop mechanism connected to the spring 72' and encircling the hose 20 is now movable relative to hose 20. Because a movable stop 80 is used, a shorter spring 72', e.g. 3-4 inches (8-10 cm), will be sufficient to fully actuate the legs to an operational position. Movable stop 80 essentially comprises a mechanical clamp which may be manually actuated to move away from or towards inspection head 16, thereby collapsing or extending, respectively, legs 14 as desired.

Specifically, to collapse legs 14 (FIG. 11), stop 80 is manually actuated to release teeth (discussed below) from engaging hose 20 to allow the biasing mechanism (comprising stop 80 and spring 72', which abuts ferrule 44) to move away from the head, thereby drawing the support legs 14 to the collapsed position shown. Conversely, to extend the legs an operator manually actuates stop 80 to move the stop, spring 72' and ferrules 44 and 46 along hose section 20 towards inspection head 16 until the support legs are fully extended to the substantially sinusoidal shapes of FIG. 12. In this embodiment the preferred free (i.e., unbiased) state of 14 is nominally straight as in FIG. 4. Spring 72' operates in this embodiment to provide compliance for extended legs 14 so they may negotiate obstacles in the pipeline by slightly collapsing. To withdraw the inspection device, the reverse procedure is followed.

A fixed stop 75, or multiple additional stops (not shown), can be provided between the ferrules 44/46 to limit the extension of legs 14 when movable stop 80 is slid to a forward position close to inspection head 16. Stop 75 is positioned to limit radial extension of legs 14 so that the legs attain a preset position which may be slightly smaller than the internal diameter of pipeline 12 to thereby limit the friction between the legs and the inner surface of the pipeline. In addition, stop 75 is located to ensure that each leg 14 attains the preferred substantially sinusoidal shape when extended.

One embodiment of a movable stop 80 is shown in cross-sectional view in FIG. 13. In this embodiment, locking levers 82 are hinged 84 to allow teeth 83 at one end thereof to engage hose 20. Levers 82 partially reside within a collar 86. Hinged levers 82 are biased via spring 72′ (FIGS. 11 & 12) which connects to (or abuts) ring 88 in engaging contact with the other end of levers 82. To release levers 82 from holding contact with hose 20, an operator manually actuates (presses) levers 82 towards hose 20 in an area adjacent to ring 88 thereby ensuring pivoting release of teeth 83 from biting contact with the hose. (Those skilled in the art will recognize that other movable stop mechanisms could also be used.)

To summarize, certain novel centralizers for an in-line pipe inspection device are described herein. The presented centralizers provide exceptional performance in terms of centralization, ease of use, and access through restricted lateral service openings in the pipe wall. Design advantages include a low profile mounting, simplistic composition (low total number of parts), variable pipe size capabilities, ease of replacement, and low cost. In addition to the described centralizer, a preferred camera assembly is also presented. This camera assembly eliminates picture degradation caused by raw signal transmission through long lengths of cable, enables existing pipe inspection hardware to be utilized to support the head unit and provides a simpler means of adapting future state-of-the-art camera technologies to the inspection device of the present invention.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

We claim:

1. A collapsible support mechanism for a pipe inspection device having an inspection head and a hose section trailing therefrom, said collapsible support mechanism comprising:
    a plurality of bendable support legs, each of said support legs having a first end and a second end, each support leg first end being pivotally secured to said inspection head;
    two ferrules encircling said hose, a first one of said two ferrules being disposed nearer to said inspection head than a second one of said two ferrules, said bendable support legs each being pivotally secured between its first end and its second end to said first ferrule, and each support leg being pivotally secured adjacent its second end to said second ferrule such that when said first and second ferrules are near said inspection head said support legs are flexibly bent and pivoted outwardly from said inspection head to support said device and when said ferrules are remote from said inspection head said support legs are collapsed towards said inspection head; and
    biasing means for maintaining said support legs in an extended position from said inspection head.

2. The collapsible support mechanism of claim 1, wherein each of said plurality of bendable support legs has a substantially sinusoidal shape when in said extended position from said inspection head.

3. The collapsible support mechanism of claim 1, wherein said extended leg maintaining means includes means for providing preformed bendable support legs each having a substantially sinusoidal shape in a free state, said support legs each being in approximately said free state when in said extended position from said inspection head.

4. The collapsible support mechanism of claim 3, wherein said maintaining means further includes a spring disposed to encircle a portion of said trailing hose section so as to engage at a first end one of said two movable ferrules, said spring also having a second end, said spring second end engaging a stop mechanism.

5. The collapsible support mechanism of claim 4, wherein said stop mechanism is at a fixed location relative to said hose.

6. The collapsible support mechanism of claim 5, wherein said spring first end contacts said second ferrule to bias said second ferrule towards said inspection head.

7. The collapsible support mechanism of claim 4, wherein said stop mechanism includes means for locking said stop mechanism at a desired location relative to said hose section.

8. The collapsible support mechanism of claim 7, wherein said locking means includes at least one hinged locking lever mechanism biased to engage said hose section.

9. The collapsible support mechanism of claim 8, wherein said locking means includes said spring, said spring second end contacting said locking lever mechanism to bias said lever mechanism to engage said hose section.

10. The collapsible support mechanism of claim 1, wherein said support legs are fabricated of bendable wire.

11. The collapsible support mechanism of claim 1, wherein said plurality of support legs comprise four bendable support legs, said support legs being symmetrically arranged about the circumference of said inspection head.

12. A collapsible centering mechanism for a pipe inspection device insertable into a pipeline through a lateral opening smaller than an internal diameter of the pipeline, said inspection device including an inspection head and a hose section trailing therefrom, said collapsible centering mechanism comprising:
    at least three bendable support legs, each support leg having a first end and a second end, each support leg being pivotally secured to said inspection head near its first end;
    a ferrule slidably encircling said hose section, each support leg being pivotally secured to said ferrule adjacent its second end, said ferrule comprising means for extending said support legs outwardly from said inspection head to support said device and means for collapsing said support legs towards said inspection head to allow the inspection device's insertion into and removal from the pipeline through the small lateral pipe opening; and a biasing mechanism for biasing said at least three support legs in said outwardly extended position from said inspection device, said extended legs providing centering of said inspection device when within said pipeline.

13. The collapsible centering mechanism of claim 12, wherein said biasing mechanism comprises a spring encircling said hose, said spring having a first end and a second end, said spring first end engaging said ferrule, said spring second end engaging a stop mechanism disposed in contact with said trailing hose section.

14. The collapsible centering mechanism of claim 13, wherein said stop mechanism is disposed at a fixed location along said hose.

15. The collapsible centering mechanism of claim 13, wherein said stop mechanism slidable relative to said hose section, said slidable stop mechanism including at least one hinged locking lever having a first end shaped to fixedly engage said hose and a second end mechanically coupled to said spring such that said spring biases said first end of said hinged locking lever into fixed engagement with said hose.

16. The collapsible centering mechanism of claim 15, wherein said slidable stop mechanism includes multiple hinged locking levers, each of said locking levers being biased to fixedly engage said hose.

17. The collapsible centering mechanism of claim 12, wherein at least two ferrules slidably surround said hose section, each support leg being pivotally secured to one of said ferrules adjacent its second end and each support leg being pivotally secured to at least one of the other of said at least two ferrules at a location intermediate its said first end and second end.

18. The collapsible centering mechanism of claim 12, wherein said at least three bendable support legs comprise four support legs, each of said support legs having a first end and a second end, each support leg first end being pivotally secured to said inspection head, each support leg second end being pivotally secured to said ferrule.

19. The collapsible centering mechanism of claim 13, wherein said at least three support legs are fabricated of a wire material.

20. Pipe inspection apparatus insertable into a pipeline for inspection or repair thereof, said apparatus comprising:

a compact pipe inspection head including a central body portion, said body portion including a viewing assembly for imaging the interior of a pipeline when said inspection head is positioned therein;

a flexible hose section connected to trail said central body portion;

multiple bendable support legs, each of said support legs having a first end and a second end, each support leg being pivotally secured to said central body portion adjacent said first end;

at least two ferrules slidably surrounding said hose section, a first one of said at least two ferrules being closer to said central body portion than a second one of said at least two ferrules, each support leg being pivotally connected adjacent said second end to said second ferrule and each support leg being pivotally connected intermediate its first end and second end to said first ferrule; and a biasing mechanism for extending said multiple bendable support legs outwardly when said inspection head is positioned within a pipeline, each said support leg defining a substantially sinusoidal shape when extending outwardly, said biasing mechanism being operable to allow collapsing of said support legs towards said central body portion and said trailing hose section.

21. The pipe inspection apparatus of claim 20, wherein said trailing hose section is sufficiently rigid so as to rotate said central body portion when said apparatus is within the pipeline to facilitate movement of the central body portion and viewing of the interior of the pipeline.

22. The pipe inspection apparatus of claim 20, wherein when said support legs are collapsed towards said central body portion, said body portion, trailing hose section and multiple support legs being sized to pass through a lateral opening of smaller diameter than an internal diameter of the pipe.

23. The pipe inspection apparatus of claim 22, wherein said viewing assembly includes a camera assembly and an illumination assembly.

24. The pipe inspection apparatus of claim 23, wherein said illumination assembly includes a plurality of lights arranged circumferentially about a lens of said camera assembly.

25. The pipe inspection apparatus of claim 20, wherein said biasing mechanism includes a spring disposed about said hose so as to engage at a first end said second ferrule and at a second end a stop mechanism.

26. The pipe inspection apparatus of claim 25, wherein said stop mechanism is at a fixed location relative to said hose.

27. The pipe inspection apparatus of claim 25, wherein said stop mechanism includes means for locking said stop mechanism at a desired location along said hose section, said stop mechanism being manually slidable along said hose section.

28. The pipe inspection apparatus of claim 27, wherein said locking means includes at least one hinged locking lever mechanism, said hinged locking lever mechanism being biased by said spring to engage said hose.

29. The pipe inspection apparatus of claim 20, wherein said support legs are fabricated of a bendable wire.

30. The pipe inspection apparatus of claim 20, wherein each of said ferrules comprises two semicircular ring portions secured together.

31. A collapsible support mechanism for a pipe inspection device having an inspection head and a cable trailing therefrom, said collapsible support mechanism comprising:

a plurality of bendable support legs, each of said support legs having a first end and a second end;

three ferrules slidably encircling said cable, a first ferrule of said three ferrules being disposed nearest to said inspection head in comparison with a second ferrule and a third ferrule of said three ferrules, said second ferrule being disposed between said first ferrule and said third ferrule, said bendable support legs each being pivotally secured adjacent said first end to said first ferrule, adjacent said second end to said third ferrule, and between its first end and its second end to said second ferrule such that when said first, second and third ferrules are slid near said inspection head, said support legs flexibly bend and pivot outwardly from said cable to support said cable and inspection head, and when said three ferrules are slid away from said inspection head, said support legs collapse towards said cable; and biasing means for selectively maintaining said support legs in their outwardly extending position from said cable.

32. The collapsible support mechanism of claim 31, wherein each of said plurality of bendable support legs has a substantially sinusoidal shape when in its outwardly extending position from said cable.

33. The collapsible support mechanism of claim 31, wherein said support legs are fabricated of bendable wire.

* * * * *